(12) United States Patent
Pocock et al.

(10) Patent No.: US 8,230,856 B2
(45) Date of Patent: Jul. 31, 2012

(54) MOUTHPIECE FOR A DEVICE FOR DISPENSING A FLUID PRODUCT

(75) Inventors: Andrew Pocock, Royston (GB); Stuart Kay, Melbourn (GB); Wayne O'Hara, Cambridge (GB); Paul Greenhalgh, Buckinghamshire (GB)

(73) Assignee: Valois SAS, Le Neubourg (FR)

( * ) Notice: Subject to any disclaimer, the term of this patent is extended or adjusted under 35 U.S.C. 154(b) by 879 days.

(21) Appl. No.: 12/160,137

(22) PCT Filed: Jan. 23, 2007

(86) PCT No.: PCT/FR2007/050679
§ 371 (c)(1),
(2), (4) Date: Nov. 10, 2008

(87) PCT Pub. No.: WO2007/085758
PCT Pub. Date: Aug. 2, 2007

(65) Prior Publication Data
US 2009/0090360 A1    Apr. 9, 2009

(30) Foreign Application Priority Data
Jan. 25, 2006    (FR) ..................... 06 50265

(51) Int. Cl.
*A61M 15/00*    (2006.01)
(52) U.S. Cl. ............... 128/203.15; 128/200.18
(58) Field of Classification Search ............. 128/204.21, 128/205.12, 203.15, 857, 859
See application file for complete search history.

(56) References Cited

U.S. PATENT DOCUMENTS

| | | | | | |
|---|---|---|---|---|---|
| 1,507,571 | A | * | 9/1924 | Barling | ........................ 131/229 |
| 2,411,692 | A | * | 11/1946 | Murano | ....................... 84/383 R |
| 3,630,196 | A | * | 12/1971 | Bird et al. | ................. 128/200.18 |
| 3,998,226 | A | * | 12/1976 | Harris | ....................... 128/203.15 |
| 4,263,907 | A | * | 4/1981 | Lindsey | .................... 128/200.18 |
| 4,739,754 | A | * | 4/1988 | Shaner | ...................... 128/203.15 |
| 5,113,855 | A | * | 5/1992 | Newhouse | ............... 128/203.12 |
| 5,829,434 | A | * | 11/1998 | Ambrosio et al. | ....... 128/203.15 |
| 6,871,647 | B2 | * | 3/2005 | Allan et al. | ............... 128/203.21 |
| 6,880,555 | B1 | | 4/2005 | Brunnberg et al. | |
| 2003/0178024 | A1 | | 9/2003 | Allan et al. | |

FOREIGN PATENT DOCUMENTS

| | | |
|---|---|---|
| CN | 1255867 A | 6/2000 |
| WO | WO 98/41256 A2 | 9/1998 |
| WO | 2005/014089 A1 | 2/2005 |
| WO | WO 2005/016424 A2 | 2/2005 |
| WO | 2006/079749 A2 | 8/2006 |

OTHER PUBLICATIONS

Chinese Office Action for Application No. 2007800003562.X, dated Jan. 10, 2011.

* cited by examiner

*Primary Examiner* — Stephen Crow
(74) *Attorney, Agent, or Firm* — Sughrue Mion, PLLC

(57) ABSTRACT

A mouthpiece (10) for a fluid dispenser device, said mouthpiece comprising a body (11) that is provided with a fluid dispenser orifice (20) through which the fluid is expelled, and said mouthpiece being characterized in that said body (11) presents a substantially convex elongate shape, with a top surface (12) incorporating said dispenser orifice (20) and extending longitudinally on two sides of said dispenser orifice (20), two lateral bearing surfaces (13) being provided laterally on two sides of said dispenser orifice (10) for receiving the lips of the user during inhalation, said top surface (12) being slightly convex and said lateral bearing surfaces (13) being slightly concave.

10 Claims, 2 Drawing Sheets

MOUTHPIECE FOR A DEVICE FOR DISPENSING A FLUID PRODUCT

The present invention relates to a mouthpiece for a fluid dispenser device, and to such a fluid dispenser device, in particular a dry-powder inhaler.

Dry-powder inhalers are well known in the prior art. Various kinds exist. A point that is common to all of the inhalers is that they include a dispenser orifice through which the user receives the dispensed powder. Generally, the dispenser orifice is provided on a mouthpiece, on or around which the user places the mouth so as to actuate the inhaler and receive the dose of powder. Depending on the structure of the inhaler, various drawbacks can appear at the mouthpiece. Firstly, some mouthpieces, in particular small mouthpieces, present a risk in that, if the user does not pay attention, the user can place the teeth at least partially in front of the opening or the dispenser orifice, thereby preventing the entire dose from being dispensed while the inhaler is being actuated. In addition, some mouthpieces are not always ergonomic, and do not guarantee good sealing with the mouth, therefore presenting both a risk of the fluid expelled by the inhaler being lost, and also a risk of head loss during inhalation, so that some of the inhalation force from the user is not directed to the inside of the apparatus. In addition, for inhalers that include cover elements that are adapted to cover and to uncover the dispenser orifice, depending on whether the cover is in the open or closed position, there is generally a risk of the user pinching one or more fingers in the mouthpiece, mainly while closing said cover elements. Documents US 2003/178024, U.S. Pat. No. 5,829,434, and WO 2005/014089 disclose prior art inhalers.

An object of the present invention is to provide a mouthpiece for a fluid dispenser device that does not have the above-mentioned drawbacks.

In particular, an object of the present invention is to provide a mouthpiece that is ergonomic, that enables good sealing with the mouth of the user, that avoids substantially all risk of the dispenser orifice being obstructed by the teeth of the user during inhalation, and that eliminates substantially all risk of fingers being pinched while manipulating the movable cover(s) of the inhaler.

Another object of the present invention is to provide a mouthpiece that is inexpensive to manufacture and to assemble and that is simple to use.

Another object of the present invention is to provide a fluid dispenser device including such a mouthpiece.

The present invention therefore provides a mouthpiece for a fluid dispenser device, said mouthpiece comprising a body that is provided with a fluid dispenser orifice through which the fluid is expelled, said body presenting a substantially convex elongate shape, with a top surface incorporating said dispenser orifice and extending longitudinally on two sides of said dispenser orifice, two lateral bearing surfaces being provided laterally on two sides of said dispenser orifice for receiving the lips of the user during inhalation, said top surface being slightly convex and said lateral bearing surfaces being slightly concave.

Advantageously, said lateral bearing surfaces extend said top surface laterally.

Advantageously, the shape of the lateral bearing surfaces oblige the user to open the mouth wide enough for the teeth not to block the dispenser orifice while the fluid is being dispensed.

Advantageously, the general shape of the body is convex.

Advantageously, said lateral bearing surfaces extend longitudinally over a central portion of said body, symmetrically about the dispenser orifice.

Advantageously, said lateral bearing surfaces extend longitudinally over the majority of said body.

Advantageously, said lateral bearing surfaces are separated by said top surface and by said dispenser orifice.

Advantageously, said dispenser orifice defines a central fluid-expulsion channel and a coaxial air channel that is disposed around said central channel so as to create a flow of air during inhalation.

The present invention also provides a fluid dispenser device including a mouthpiece as described above.

Advantageously, said mouthpiece is snap-fastened on a body of said device.

Advantageously, the device includes at least one cover element that is movable between a closed position in which it covers the dispenser orifice and an open position in which it uncovers the dispenser orifice, the shape of said mouthpiece preventing the fingers of the user from being pinched while said at least one cap element is being opened and/or closed.

Advantageously, said dispenser is a dry-powder inhaler.

These characteristics and advantages of the present invention, and others, appear more clearly from the following detailed description of a particular embodiment thereof, given by way of non-limiting example, and with reference to the accompanying drawings, in which.

Figure 1:
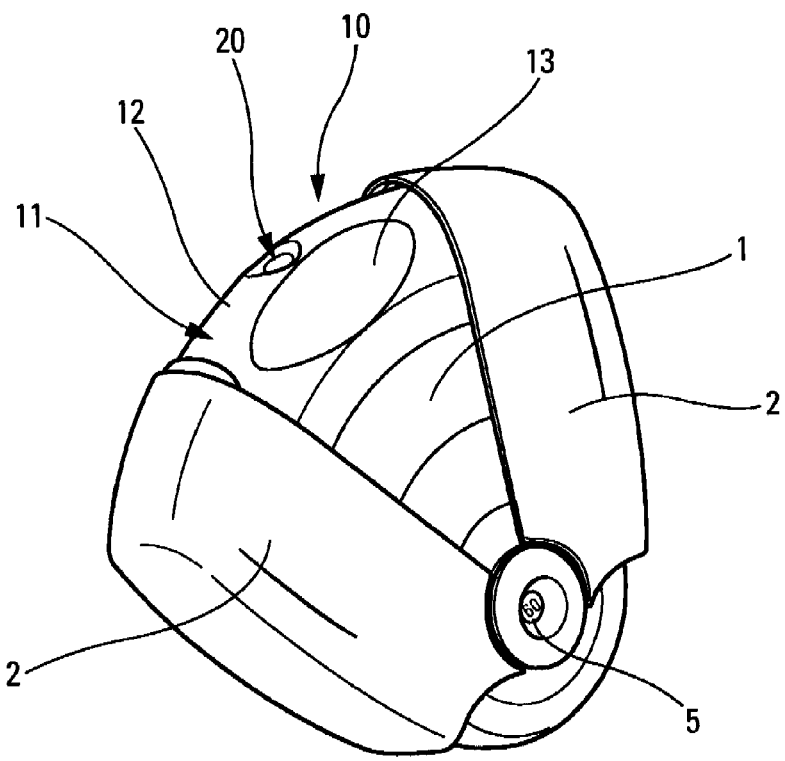
FIG. 1 is a diagrammatic perspective view of a dry-powder inhaler constituting a particular embodiment of the present invention.

FIG. 1 shows an example of a dry-powder inhaler to which the present invention applies. However, naturally the inhaler shown in FIG. 1 is non-limiting, and, on the contrary, the mouthpiece of the invention could apply to any type of dry-powder inhaler of any shape. In general, the mouthpiece of the present invention applies to dispensing any type of fluid, i.e. liquid, paste, powder, or gas.

The inhaler shown in FIG. 1 includes a body 1 on which there are assembled two movable cover elements 2 that, in this embodiment, pivot about a common pivot axis between an open position (shown in FIG. 1), in which a dispenser orifice 20 of the inhaler is uncovered, and a closed position (not shown), in which the two movable cover elements 2 are brought together so as to cover the dispenser orifice. A dose counter can advantageously be provided in the inhaler, and the doses can be displayed in a window 5 that can, for example, be provided on the pivot axis of the two cover elements 2, as shown diagrammatically in FIG. 1.

Figure 4:
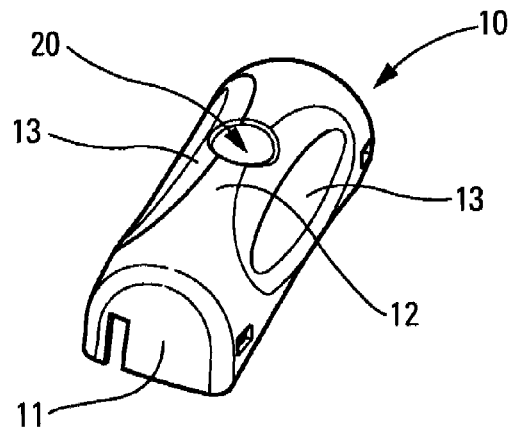
FIG. 4 is a diagrammatic perspective view of a mouthpiece constituting an advantageous embodiment of the present invention.
Figure 5:
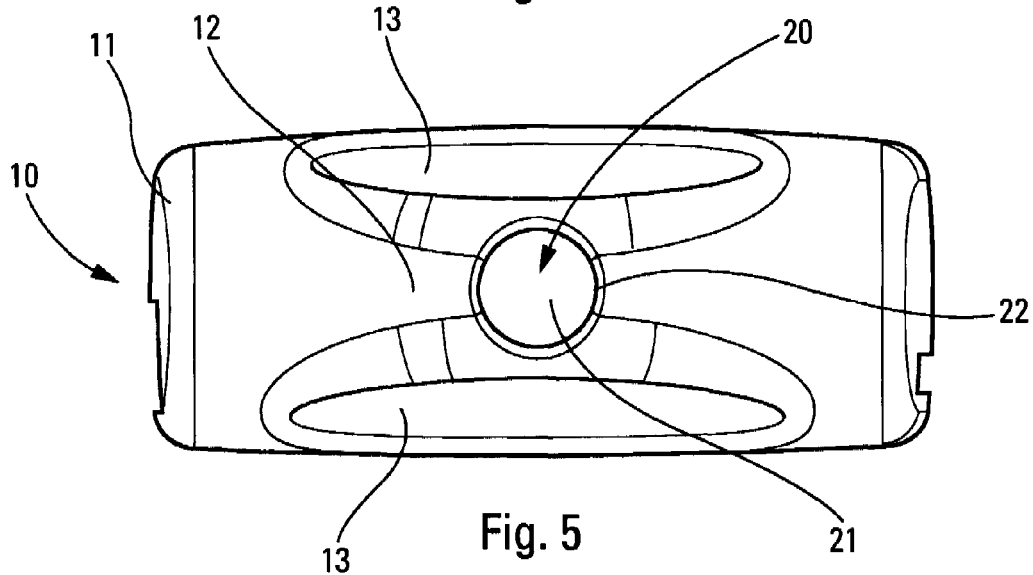
FIG. 5 is a larger-scale plan view of the FIG. 4 mouthpiece.
Figure 6:
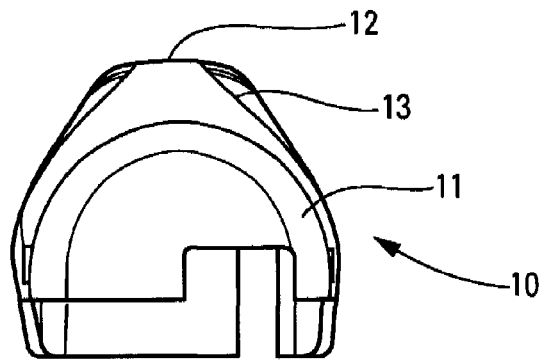
FIG. 6 is a side view in cross-section of the mouthpiece in FIGS. 4 and 5.

FIGS. 4 to 6 show an advantageous embodiment of the mouthpiece of the present invention. With reference to FIGS. 4 to 6, the mouthpiece 10 comprises a body 11 that is provided with a fluid dispenser orifice 20. For an inhaler, the fluid is generally dry powder mixed with a flow of air. In the context of a "passive" inhaler, the flow of air is the flow of air that is created by the user inhaling. For an "active" inhaler, a flow of compressed air is used to expel the powder when the inhaler is actuated. As shown in particular in FIG. 4, the body 11 presents a longitudinally elongate shape that is substantially rounded or convex in the transverse direction, with a top surface 12 that incorporates the dispenser orifice 20, preferably at its center. In general, the mouthpiece 10 is preferably symmetrical about said dispenser orifice 20. The top surface 12 extends longitudinally on either side of said dispenser orifice 20, and advantageously as far as the lateral edges of the body 11. It should be observed that the top surface 12 is also slightly humped or convex in the longitudinal direction, thereby imparting a flattened rounded shape to the mouthpiece 10. On either side of the dispenser orifice 20, in the transverse or lateral direction, the body 11 includes two lateral bearing surfaces 13 that are respectively provided laterally on each side of said dispenser orifice 20. Each of the lateral bearing surfaces 13 is for receiving a lip of the user during inhalation. The lateral bearing surfaces 13 are slightly concave, in particular in the transverse direction, so as to form slight hollows that are adapted to position the lips of the user properly, when said user places them on the mouthpiece. As shown in particular in the figures, the lateral bearing surfaces 13 extend said top surface 12 laterally, and they are preferably separated from each other by the top surface 12 and by the dispenser orifice 20. In this way, when the user places the mouth on the mouthpiece 10, the spacing between the two lateral bearing surfaces 13 obliges the user to open the mouth wide enough to avoid the teeth obstructing the dispenser orifice 20, even in part, during inhalation. In addition, the plane or slightly concave surface of the lateral bearing surfaces 13 is ergonomic, ensuring good sealing with the mouth of the user on the mouthpiece 10 during inhalation. For a passive-type inhaler, this avoids unnecessary head loss during inhalation, and guarantees that as much as possible of the user-created inhalation flow is used to expel the powder contained in the inhaler. The spacing and the depth of the lateral bearing surfaces 13 also guarantee that the dispenser orifice is positioned inside the mouth, beyond the teeth, but without the dispenser orifice 20 being formed on a projecting portion of the mouthpiece 10.

The lateral bearing surfaces 13 advantageously extend longitudinally over a central portion of said body 11, preferably over the major part thereof, as shown in particular in FIG. 5. Advantageously, the two lateral bearing surfaces 13 are completely symmetrical to each other, about the dispenser orifice 20.

The dispenser orifice 20 advantageously defines a central powder-expulsion channel 21 and an air channel 22 that is coaxial relative to said central channel 21, and that is disposed around said central channel. The air channel 22 makes it possible to create the flow of air during inhalation, and, for an inhaler that is triggered by the user inhaling, it makes it possible to actuate the trigger system, as described below with reference to FIGS. 2 and 3.

With reference once again to FIG. 1, it should be observed that the cover elements 2 that are movable about the body 1 of the inhaler and about the mouthpiece 10, include a top surface of convex shape that is substantially adapted to the shape of the mouthpiece, in particular at its top surface 12. In this way, while said cover elements 2 are being displaced between the open and closed positions, no gap is created as a result of the presence of the mouthpiece 10, such that the fingers of the user do not risk being pinched while manipulating the cover elements 2. In general, the mouthpiece of the present invention does not include any projecting portion that risks creating a gap that could receive the user's fingers while the device is being actuated.

Figure 2:
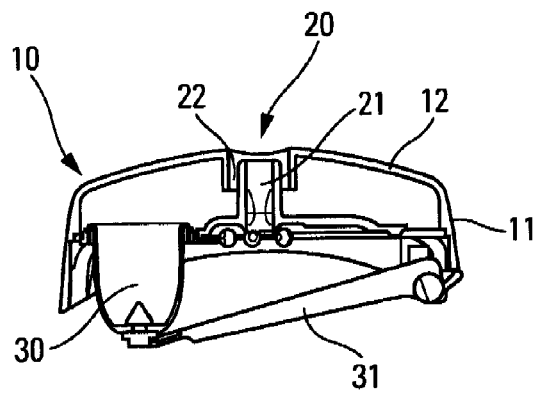
FIG. 2 is a fragmentary and diagrammatic section view of an inhalation-trigger system constituting a particular embodiment, and shown in its position before inhalation.
Figure 3:
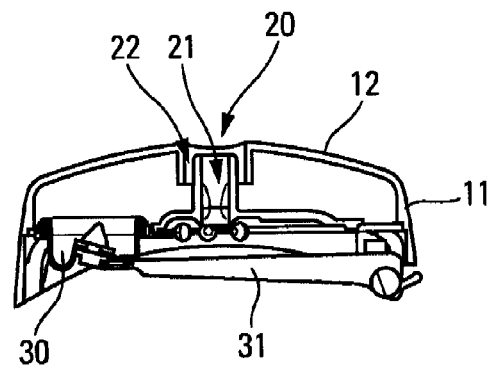
FIG. 3 is a view similar to the view in FIG. 2, shown after inhalation.

Reference is made below to FIGS. 2 and 3 which show an inhalation-trigger system of an inhaler constituting an advantageous embodiment. The system advantageously includes a deformable chamber 30, also referred to as a diaphragm, that, when the user inhales through the mouthpiece 20, deforms so as to displace a rod 31 that is connected to said diaphragm 30, thereby triggering the expulsion of a dose of powder. With reference to FIGS. 2 and 3, it should be observed that the air channel 22 disposed in the dispenser orifice 20 around the central powder-expulsion channel 21 is connected directly to said deformable chamber 30, thereby guaranteeing that the device is triggered reliably. FIGS. 2 and 3 also show the longitudinally humped or convex shape of the top surface 12 of the mouthpiece, and the fact that the dispenser orifice 20 of the mouthpiece is not formed on a portion that projects relative to said top surface 12 of the body 11.

Although the invention is described above with reference to a particular embodiment thereof, naturally it is not limited by the examples shown. On the contrary, any useful modification could be applied thereto by a person skilled in the art, without going beyond the ambit of the present invention, as defined by the accompanying claims.

The invention claimed is:

1. A fluid dispenser device, comprising:
a mouthpiece for a fluid dispenser device, said mouthpiece comprising a body that is provided with a fluid dispenser orifice through which the fluid is expelled, said body presents a substantially convex elongate shape, with a top surface incorporating said dispenser orifice and extending longitudinally on two sides of said dispenser orifice, two lateral bearing surfaces provided laterally on two sides of said dispenser orifice for receiving the lips of the user during inhalation, said top surface slightly convex and said lateral bearing surfaces slightly concave;
said dispenser further comprising at least one cover element that is movable between a closed position in which the cover element covers the dispenser orifice-and an open position in which the cover element uncovers the dispenser orifice, the shape of said mouthpiece preventing fingers of the user from being pinched while said at least one cover element is opened and/or closed.

2. The device according to claim 1, in which said lateral bearing surfaces extend said top surface laterally.

3. The device according to claim 1, in which the general shape of the body is convex.

4. The device according to claim 1, in which said lateral bearing surfaces extend longitudinally over a central portion of said body, symmetrically about the dispenser orifice.

5. The device according to claim 4, in which said lateral bearing surfaces extend longitudinally over the majority of said body.

6. The device according to claim 1, in which said lateral bearing surfaces are separated by said top surface and by said dispenser orifice, such that the user is obliged to open the mouth wide enough for the teeth not to block the dispenser orifice while the fluid is being dispensed.

7. The device according to claim 1, in which said dispenser orifice defines a central fluid-expulsion channel and a coaxial air channel that is disposed around said central channel so as to create a flow of air during inhalation.

8. The device according to claim 1, in which said mouthpiece is snap-fastened on a body of said device.

9. The device according to claim 1, in which said dispenser is a dry-powder inhaler.

10. The device according to claim 1, wherein the cover element has a top surface that is convex conforming to a corresponding top surface of the mouthpiece.

* * * * *